(12) United States Patent
Van Rooyen et al.

(10) Patent No.: US 9,456,987 B2
(45) Date of Patent: Oct. 4, 2016

(54) CAPSULE WITH INTERNAL DIAPHRAGM

(71) Applicant: Binutra, Inc., El Segundo, CA (US)

(72) Inventors: Jacques Van Rooyen, Cape Town (ZA); Duncan E. B. Miller, Cape Town (ZA)

(73) Assignee: Binutra, Inc., El Segundo, CA (US)

( * ) Notice: Subject to any disclaimer, the term of this patent is extended or adjusted under 35 U.S.C. 154(b) by 128 days.

(21) Appl. No.: 13/856,334

(22) Filed: Apr. 3, 2013

(65) Prior Publication Data

US 2014/0302133 A1    Oct. 9, 2014

(51) Int. Cl.
*A61K 9/48* (2006.01)

(52) U.S. Cl.
CPC .................... *A61K 9/4808* (2013.01)

(58) Field of Classification Search
CPC ............. A61K 9/4808; A61K 9/4833; A61K 9/4816; A61K 9/4825; A61J 3/072; A61J 3/071; A61J 3/074; A61J 3/07; B29L 2031/7174; Y10S 53/90; Y10S 264/37
See application file for complete search history.

(56) References Cited

U.S. PATENT DOCUMENTS

| | | |
|---|---|---|
| 961,936 A | 6/1910 | Colton et al. |
| 1,510,260 A | 9/1924 | Cyrenius |
| 1,861,047 A | 5/1932 | Colton |
| 2,584,622 A | 2/1952 | Scherer et al. |
| 2,738,827 A | 3/1956 | Roll |
| 2,936,493 A | 5/1960 | Scherer |
| 3,186,910 A | 6/1965 | Glassman |
| 3,200,556 A | 8/1965 | Ackley |
| 3,228,789 A | 1/1966 | Glassman |
| 3,324,902 A | 6/1967 | Lense |
| 3,518,340 A | 6/1970 | Raper |
| 3,538,677 A | 11/1970 | Amoroso et al. |
| 3,886,940 A | 6/1975 | Hunger |

(Continued)

FOREIGN PATENT DOCUMENTS

| | | |
|---|---|---|
| CA | 763203 A | 7/1967 |
| CA | 781906 A | 4/1968 |

(Continued)

OTHER PUBLICATIONS

Capsule Size Chart by Torpac Inc. (2000, pp. 1-3).*

(Continued)

*Primary Examiner* — Aradhana Sasan
(74) *Attorney, Agent, or Firm* — Morrison & Foerster LLP

(57) ABSTRACT

A capsule of, for instance, hard gelatin for holding a substance such as medicine, food supplements or similar materials includes a capsule body having a closed and an opposed open end with a predetermined length defined between the ends. A diaphragm having a closed end and an opposed open end and a predetermined length there between seals off the body and provides a first compartment to hold a first medicine, food supplement, etc. A cap is applied to the body as is conventional in capsules. The space between the inner portion of the cap and the diaphragm defines a second compartment for holding a second medicine, food supplement, etc. The contents of each compartment may be wet or dry (e.g., powder or liquid.) This two-compartment capsule has particular relationships between the length along an axis of the capsule of the diaphragm to that of the body, and particular dimensional parameters relating to the sidewall contact seal between the outer portion of the diaphragm and the inner wall of the body, to provide adequate capsule sealing and stability during and after manufacture.

18 Claims, 7 Drawing Sheets

(56) References Cited

U.S. PATENT DOCUMENTS

| | | |
|---|---|---|
| 3,893,278 A | 7/1975 | Lewis |
| 3,927,195 A | 12/1975 | Messora |
| 3,978,640 A | 9/1976 | Crossley et al. |
| 4,007,942 A | 2/1977 | Hofliger |
| 4,196,565 A | 4/1980 | Bodenmann et al. |
| 4,231,211 A | 11/1980 | Strampfer et al. |
| 4,403,461 A | 9/1983 | Goutard et al. |
| 4,450,877 A | 5/1984 | Walker et al. |
| 4,522,666 A | 6/1985 | Wittwer |
| 4,543,138 A | 9/1985 | Bollinger et al. |
| 4,609,417 A | 9/1986 | Smith |
| 4,627,850 A | 12/1986 | Deters et al. |
| 4,656,066 A | 4/1987 | Wittwer |
| 4,659,415 A | 4/1987 | Shimokawa et al. |
| 4,662,155 A | 5/1987 | Chasman |
| 4,667,498 A | 5/1987 | Sauter |
| 4,724,019 A | 2/1988 | Brown et al. |
| 4,793,493 A | 12/1988 | Makiej, Jr. |
| 4,899,516 A | 2/1990 | Krieger et al. |
| 4,964,262 A | 10/1990 | Moser et al. |
| 4,991,377 A | 2/1991 | Marchesini |
| 4,993,137 A | 2/1991 | Muto et al. |
| 5,074,426 A | 12/1991 | Goodhart et al. |
| 5,081,822 A | 1/1992 | Boyd et al. |
| 5,110,597 A | 5/1992 | Wong et al. |
| 5,111,642 A | 5/1992 | Chiari |
| 5,188,688 A | 2/1993 | Boardman et al. |
| 5,223,265 A | 6/1993 | Wong |
| 5,507,640 A | 4/1996 | Gilmer et al. |
| 5,674,530 A | 10/1997 | Amidon et al. |
| 5,698,155 A | 12/1997 | Grosswald et al. |
| 5,800,422 A | 9/1998 | Dong et al. |
| 5,897,874 A | 4/1999 | Stevens et al. |
| 5,938,654 A | 8/1999 | Wong et al. |
| 5,967,405 A | 10/1999 | Hanauska |
| 5,976,571 A | 11/1999 | Crison et al. |
| 6,303,144 B1 | 10/2001 | Omura |
| 7,163,693 B1 | 1/2007 | Clarke et al. |
| 7,523,596 B2 | 4/2009 | Dovesi |
| 7,645,407 B2 | 1/2010 | Cade et al. |
| 7,694,497 B2 | 4/2010 | Tagliavini et al. |
| 8,621,825 B2 | 1/2014 | Schmied et al. |
| 2002/0098172 A1 | 7/2002 | Udell et al. |
| 2003/0029558 A1 | 2/2003 | Hochrainer et al. |
| 2003/0194429 A1 | 10/2003 | Miller et al. |
| 2003/0194431 A1* | 10/2003 | Miller et al. .............. 424/451 |
| 2004/0081689 A1 | 4/2004 | Dunfield et al. |
| 2004/0170679 A1 | 9/2004 | Schurig et al. |
| 2005/0008690 A1 | 1/2005 | Miller |
| 2006/0064943 A1 | 3/2006 | Trebbi et al. |
| 2006/0159745 A1 | 7/2006 | Baksh |
| 2006/0188607 A1 | 8/2006 | Schramm et al. |
| 2007/0065502 A1 | 3/2007 | Baksh |
| 2007/0087048 A1 | 4/2007 | Abrams et al. |
| 2008/0102113 A1 | 5/2008 | Rosenberg |
| 2008/0236106 A1 | 10/2008 | Trebbi et al. |
| 2009/0162430 A1 | 6/2009 | Mahmoud et al. |
| 2009/0205748 A1 | 8/2009 | Ansaloni |
| 2010/0009027 A1 | 1/2010 | Cade et al. |
| 2010/0209389 A1 | 8/2010 | McInnes et al. |
| 2010/0212261 A1 | 8/2010 | Boldis et al. |
| 2011/0088355 A1 | 4/2011 | Fulper |
| 2012/0035528 A1 | 2/2012 | Coppeta et al. |
| 2012/0039998 A1 | 2/2012 | Valla et al. |
| 2012/0049410 A1 | 3/2012 | Altamar et al. |
| 2013/0186561 A1 | 7/2013 | Van Rooyen et al. |
| 2013/0233467 A1 | 9/2013 | Van Rooyen et al. |

FOREIGN PATENT DOCUMENTS

| | | |
|---|---|---|
| DE | 27 29 007 A1 | 1/1979 |
| EP | 0 308 637 A1 | 3/1989 |
| EP | 1 459 725 A1 | 9/2004 |
| FR | 1454013 A | 8/1966 |
| GB | 1027779 A | 4/1966 |
| GB | 1027780 A | 4/1966 |
| GB | 2002316 A | 2/1979 |
| NL | 7610038 A | 3/1978 |
| WO | WO-94/03365 A1 | 2/1994 |
| WO | WO-2007/047371 A2 | 4/2007 |
| WO | WO-2007/047371 A3 | 4/2007 |
| WO | WO-2008/113368 A1 | 9/2008 |
| WO | WO-2013/050973 A1 | 4/2013 |
| WO | WO-2013/050974 A1 | 4/2013 |

OTHER PUBLICATIONS

International Search Report mailed Mar. 22, 2013, for PCT Patent Application No. PCT/IB2012/055372 filed on Oct. 5, 2012, four pages.

International Search Report mailed Feb. 12, 2013, for PCT Patent Application No. PCT/IB2012/055374 filed on Oct. 5, 2012, four pages.

Written Opinion of the International Searching Authority mailed Mar. 22, 2013, for PCT Patent Application No. PCT/IB2012/055372 filed on Oct. 5, 2012, five pages.

Written Opinion of the International Searching Authority mailed Feb. 12, 2013, for PCT Patent Application No. PCT/IB2012/055374 filed on Oct. 5, 2012, six pages.

* cited by examiner

CAPSULE WITH INTERNAL DIAPHRAGM

FIELD OF THE INVENTION

This disclosure relates to capsules, for instance, gelatin-type capsules of the type commonly used for administering medicines, dietary supplements, etc.

BACKGROUND

Capsules for holding medicines, dietary supplements, etc., are very well known and have been in commercial use for many years for human and veterinary use. They are typically made of a digestible gelatin-like material and contain a medicine in liquid or powder form or a dietary supplement, such as vitamins, fish oil, etc. in a single internal cavity (compartment). Moreover, such capsules are typically manufactured in certain standard sizes referred to as capsule size designated by numerals, such as 000, 00, etc. One of the most common sizes is the 00 capsule. This disclosure is generally of a capsule of 00 size, but this is not at all limiting but is merely illustrative. The typical 00 size capsule, in common with other capsules, has a standardized nominal volume. For instance, a 00 capsule has a volume of approximately 0.95 milliliters. The typical weight of such a typical capsule is 119 milligrams. Such capsules typically have two parts, a cap and a body, which are bonded together. The typical nominal length of the cap (along the long axis of the capsule) is 11.8 mm, plus or minus 0.4 mm. The length of the body (also as a separate component) is 20.2 mm plus or minus 0.4 mm. The overall assembled length of such a capsule is 23.5 mm plus or minus 0.4 mm. The outside diameter of the cap is typically 8.5 mm plus or minus 0.03 mm and the outside diameter of the body, which is slightly smaller than that of the cap, since typically the cap fits over the body when assembled, is 8.22 mm, plus or minus 0.03 mm. Other sizes of capsules each have their own nominal dimension Most such capsules only contain a single ingredient in a single compartment. However, it is known in the field to provide capsules which hold two ingredients in two separate compartments. These are used when the ingredients should not be mixed together inside the capsule. For an example of same see FIG. 1, which is the sole figure in Netherlands patents No. 7,610,038 issued to Tapanahony N. V. on 13 Mar. 1978. This shows in a cross section such a two-compartment capsule 10 having a body 11, which defines a first chamber or compartment holding a first ingredient B. The inner wall of the body portion is indicated at 12. Extending into the body is what may be referred to as a diaphragm 16, which includes a lower curved portion and which holds in a second compartment defined by its upper surface a second ingredient A. The inner surface of the diaphragm is indicated at 17. The cap 15 is shown as having a typical curved upper end and an inner surface 14. The upper end of the diaphragm is indicated at 13. Typically ingredients A and B are different materials.

A different two-compartment capsule is shown similarly in cross-section in present FIG. 2 from French patent No. 1,454,013 issued to Pluripharm on $22^{nd}$ of August 1966. This similarly has a body 23, which contains a first ingredient C and an upper compartment defined by the diaphragm 24 which contains the second ingredient D with the cap 25 extending over the outside of the body p 23. Here the diaphragm 24 sidewalls extend all the way up to contact the inner surface of the cap 25 to contain ingredient D.

However, such two-compartment capsules are not believed to be in wide (if any) commercial use likely due to the difficulties of successfully making and filling same in large volume. The present inventors, moreover, have determined there are several technical deficiencies with these known two-compartment capsules. They identified two such aspects, which it is believed are not properly addressed up to now. One is during assembly of the capsule (when it is being filled with the ingredients) to provide proper alignment of the diaphragm that results in an even edge at the top of the capsule/diaphragm mouth, allowing for a good seal surface at both at the tops and the sides of the diaphragm. This technical problem may be addressed by the sidewalls of the diaphragm 24 in FIG. 2 extending to the top of the cap. Further, the present inventors have determined that the sidewall contact between the diaphragm and the body in the prior art is not sufficient to provide proper overall integrity and robustness of a capsule during and after filling and assembly of the capsule.

SUMMARY

Therefore, the present inventors have determined that an improved two-compartment capsule includes, as is conventional, a cap, diaphragm and body. The general configuration of this capsule is similar to those known in the field. However, certain particular dimensions and dimension parameters of the diaphragm relative to the body have been determined by them to be important to solve the above indicated technical deficiencies. Specifically, a ratio of the length of the body of the capsule to the length of the diaphragm along the length axis of the entire capsule has been found to be optimized in a range of 2.0 to 2.9. Specifically, in the case of a 00 size capsule having a body of approximately 20.2 mm long, the length of the diaphragm is approximately 8.5 mm and in the range of 7 to 10 mm. For such a capsule with a length of 8.5 mm, this ratio is 20.2 to 8.5, equal to approximately 2.37. For other capsule sizes, this ratio and possibly the length would also apply, since some of the other capsules are significantly larger or smaller in terms of length. Further, a particular length of the sidewall contact region between the straight cylindrical walls of the diaphragm and the inner surface of the body has been found to be optimized at a length in the range of 4.5 to 7 mm. For a size 00 capsule, this sidewall contact region is approximately 6 mm in length.

It was found that a shorter diaphragm (outside the above ranges) is unstable and thus tends to rotate inside the body during insertion of the diaphragm into the capsule, prior to capsule sealing. Such a shorter diaphragm does not hold sidewall integrity even after the diaphragm and body are bonded together and so the resulting capsule may not hold together. This instability is made worse after capsule filling, when the capsule is stored and shipped at different temperatures which may cause expansion of the air/gas/liquid inside the capsule resulting in stress on the capsule and the possibility of capsule leakage or rupture. Further, a much longer in length diaphragm (outside the above ranges) has been found to cause problems, especially when the lower compartment, defined between the diaphragm and the body, is filled with a liquid, topped off with a gas, in which case the pressure and sidewall friction of the diaphragm insertion becomes great and the internal pressure builds up, causing the likelihood of a rupture of the capsule during its assembly.

So this particular configuration provides optimum alignment of the diaphragm during assembly which results in an even edge at the top of the capsule/diaphragm mouth along with a good seal surface both at the rim and the sides of the diaphragm. In one embodiment, both the sidewall and rim of the diaphragm are sealed to the body. Given this configuration, of the total length of the diaphragm, approximately 2.5 mm is the curved or hemispherical section and the remainder of the length is allocated to its straight sidewalls. This sidewall length acts as both a support and a sidewall seal. It has been found that if the length of this sidewall contact with the body is less than approximately 4.5 mm, the body-diaphragm seal is likely to fail. Of course, having too much at length of this sidewall contact area would severely reduce the volume at the lower portion that is the lower compartment of the capsule, thus reducing the capsule's utility. For the above described diaphragm with a length of 8.5 mm and sidewall that is 6 mm long (hence the length of the hemispherical portion of the diaphragm is 2.5 mm long), a ratio of the length of the diaphragm's sidewall contact area to the overall length of the body is approximately 6 mm to 20.2 mm, a ratio of approximately 0.3. Generally this ratio is in the range of 0.22 to 0.37. A range for this sidewall length for an exemplary capsule is 4.5 to 7.5 mm. Note that in accordance with the invention, the differences from a standard 00 (or other size) capsule lie in the diaphragm and its relationship to the body, whereas the cap is essentially conventional.

DETAILED DESCRIPTION

Figure 1:
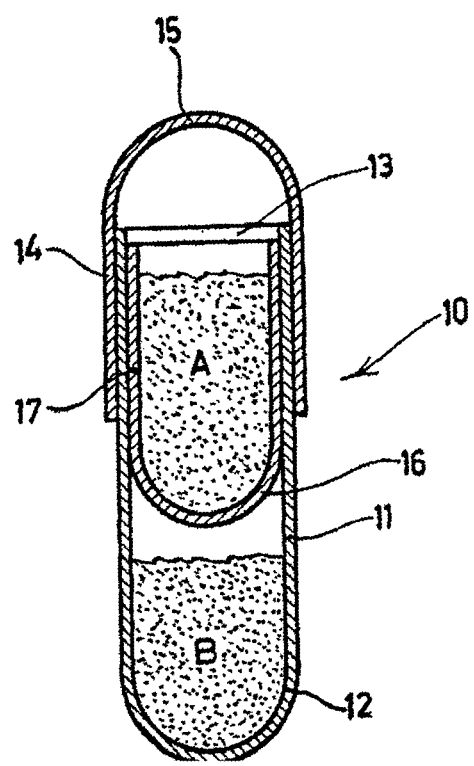
FIG. 1 shows in the prior art a cross-sectional view of a prior art two-compartment capsule.
Figure 2:
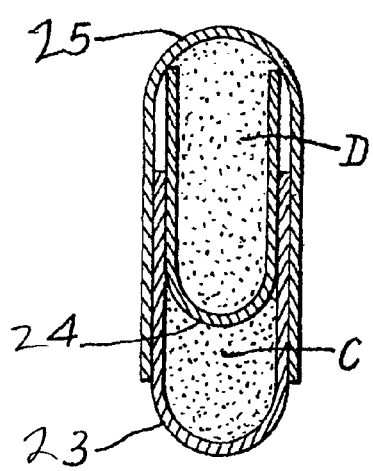
FIG. 2 shows in the prior art another version of a two-compartment capsule.
Figure 3A:
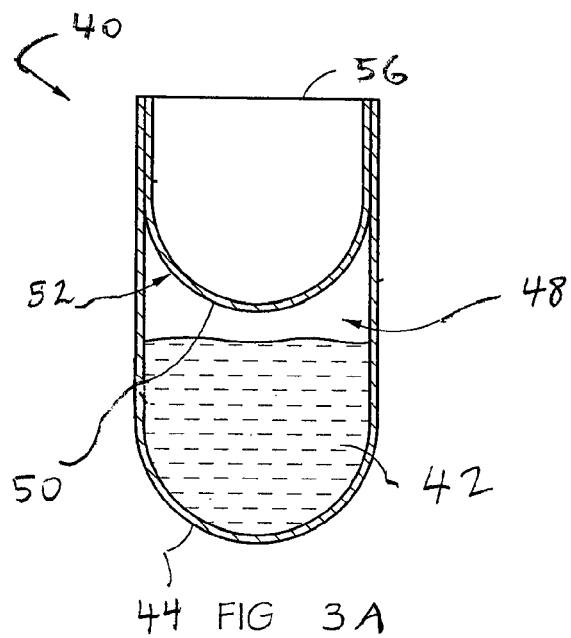
FIG. 3A shows in accordance with the invention in a cross-sectional view the diaphragm and body of a two-compartment capsule with the lower compartment partly filled.
Figure 3B:
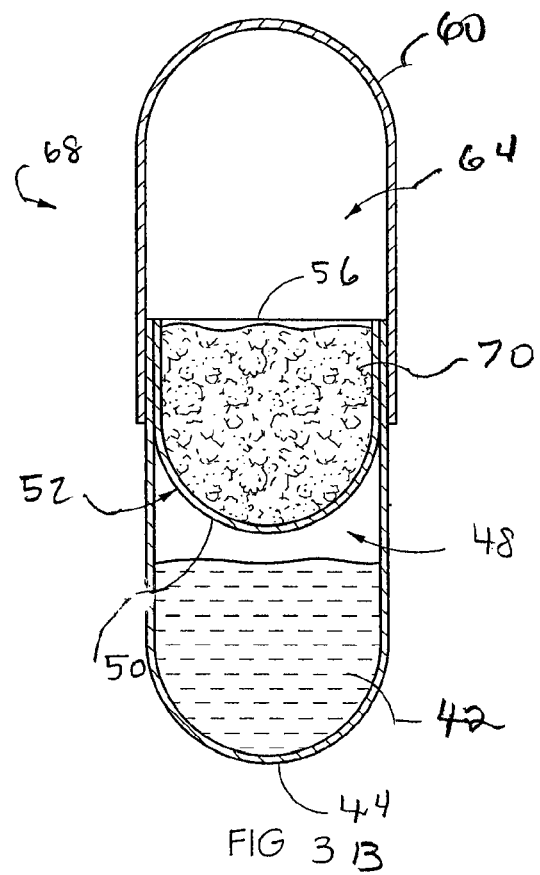
FIG. 3B shows in a cross-sectional view the body portion of a capsule 3A with the cap portion also provided.

Present FIGS. 3A and 3B show, respectively, a sectional side view of the body portion (body and diaphragm) of a capsule in accordance with the present invention and a sectional side view of the capsule, including the cap. These figures are respectively similar to FIGS. 1 and 2 of International application No. PCT/IB2012/055374 filed 5 Oct. 2012 entitled "A Method and Apparatus for Manufacturing a Capsule" commonly invented with the present application. However, that disclosure does not indicate the particular dimensionality or certain other aspects of the capsule itself, which are disclosed herein. This international patent application and commonly invented International patent application PCT/IB2012/55372 filed 5 Oct. 2012, entitled "A Method and Apparatus for Manufacturing Capsules" are both incorporated herein by reference in their entireties.

FIG. 3A shows in a cross-sectional sideview the body portion 40 (without the cap) of a capsule in accordance with the present invention. This is typically in the form of a digestible hard gelatin capsule for holding a substance (ingredient) 42 such as fish oil in its lower compartment. However, the nature of the ingredient held, of course, is not limiting and this is merely illustrative. The ingredients may be wet or dry (powder or liquid) and may as usual include excipients (inactive carriers) which are wet or dry. Typically, of course, fluids such as fish oil must be held in a liquid-tight chamber 48 defined by the body 44. The lower chamber 48 includes in some embodiments in its upper portion a low-pressure (sub-atmospheric) gas which will not react with the ingredient 42, such as nitrogen gas. Note that certain ingredients and/or excipients are unstable and the non-reactive gas may be provided to preserve such unstable materials. Separating the lower compartment from the upper compartment is a diaphragm 50 made of a similar material as the body 44 (e.g., hard gelatin) and which is originally fabricated conventionally as a separate component from the body 44. Conventionally, body 44 is typically in the form of a hollow cylindrical tubular body defining its closed-end as indicated at the lower portion of the drawing and an opposed upper end 52 defined by the lower wall of the diaphragm 50. The upper end 56 of the capsule body portion assembly 40 is open here, that is not sealed off.

Figure 3C:
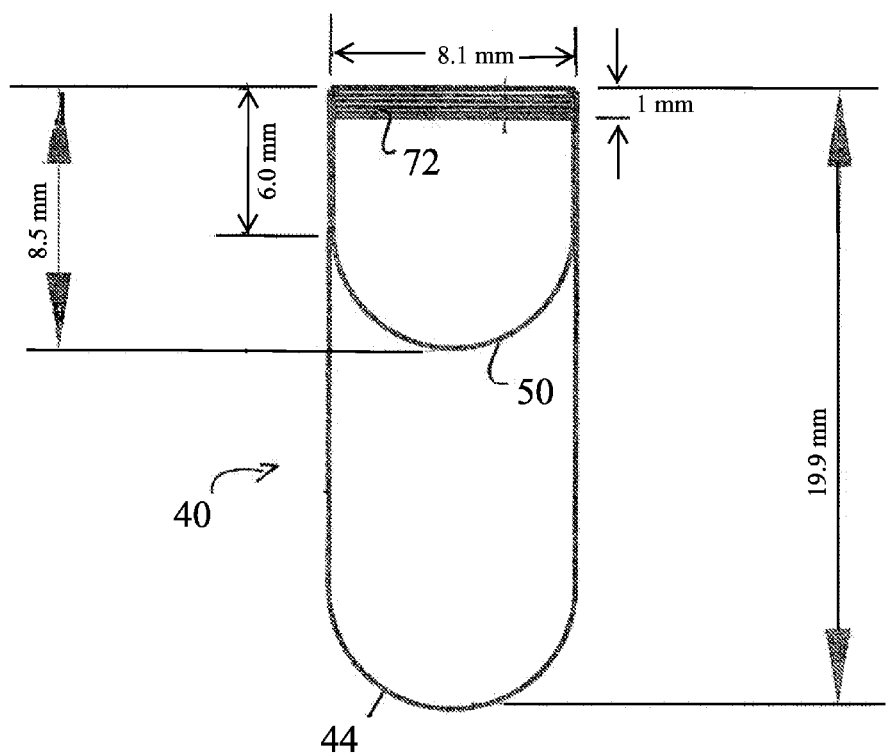
FIG. 3C shows detail of the FIG. 3B body portion.

FIG. 3B shows the fully assembled capsule 68 including the body portion of FIG. 3A with the addition of the cap 60 defining the upper chamber 64. Also shown is the second ingredient 70 (here illustrated as a powder but that is not limiting), located in the upper compartment 64. FIG. 3C shows relevant dimensions for one embodiment, in this case for a 00 capsule, for the capsule body portion of FIG. 3A, including the length of the body portion and diaphragm, the length of the sidewall contact area along the straight portions of the diaphragm and the body inner surface, and the other relevant parameters. FIG. 3C shows the body portion after it is sealed to the diaphragm, where the sealing process creating the sealed region 72 slightly shortens the length of the body portion compared to that of the unsealed body 44 by itself. Again, this is for a 00 size capsule, which is merely illustrative.

Figure 4:
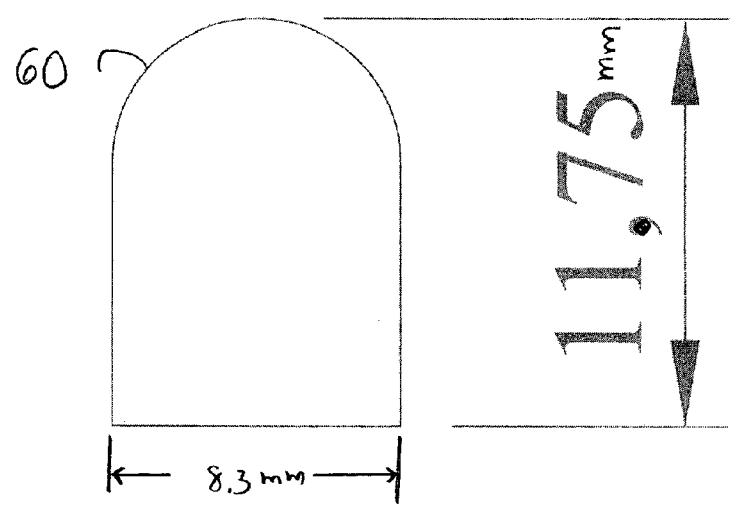
FIGS. 4A, 4B and 4C respectively show the cap, diaphragm and body of the capsule of FIG. 3B separately.
Figure 4:
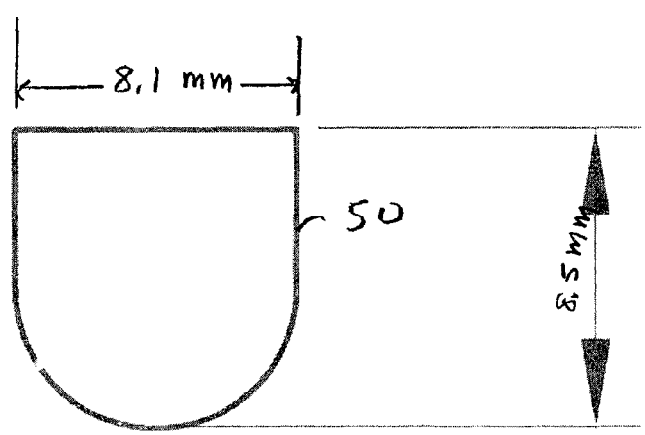
Figure 4:
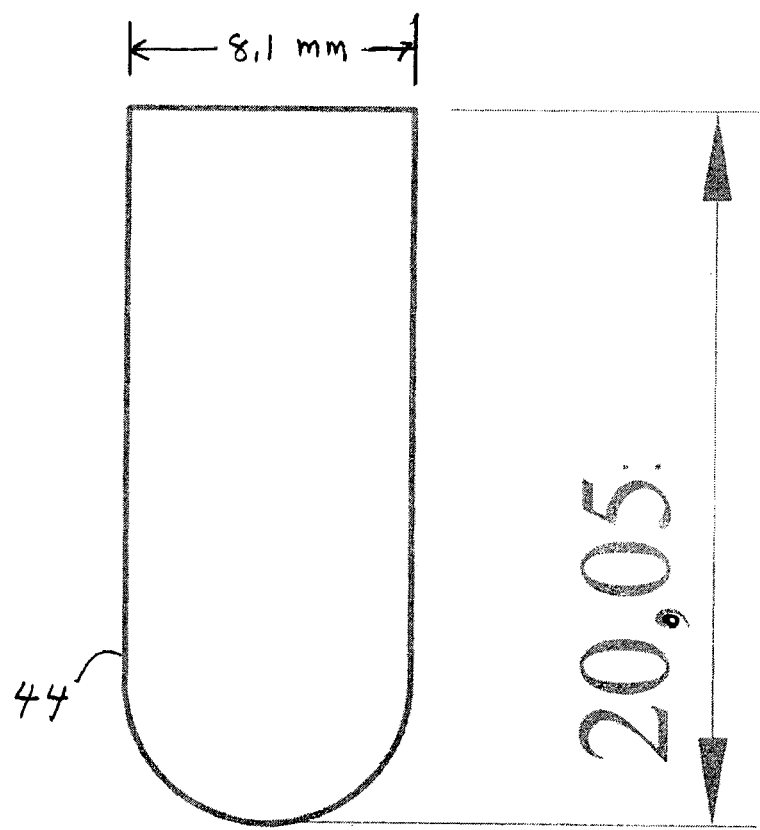

FIGS. 4A, 4B and 4C respectively show examples of the three capsule components of FIG. 3B, which are the cap 60, the diaphragm 50 and the body 44 with exemplary dimensions, to illustrate these in disassembled form. The thickness of the wall of each component is conventionally about 0.2 mm.

Assembling and filling single compartment capsules is well known in the field, as is manufacturing their components, so further details regarding this are not disclosed here. The above-referenced international applications describe ways to fill and bond together the components of such two-compartment capsules, but that is merely exemplary and other techniques can be used for filling and assembly, as known in the field. Hence the filling and sealing of the present capsules is not limited to the methods described in those international applications.

Often the capsule filler organization does not fabricate its own capsule components, but in some cases they do. In other cases, these components are purchased by the filler organization. It is therefore contemplated that in accordance with the invention, various embodiments include (1) provision of the three separate capsule components shown in FIGS. 4A, 4B, 4C; (2) the body portion assembly of FIG. 3A, which shows the body portion filled; and the final assembled, sealed and (3) the filled capsule of FIG. 3B including the upper cap also affixed to the body portion and filled with the second ingredient 70.

So as explained above, the relevant relationship and parameters of the present capsules is that in one aspect a ratio of the length of the body of the capsule (along its length axis), to the overall length of the diaphragm along the same axis is in the range of 2.0 to 2.9, with an exemplary ratio value of approximately 2.37. Again, while this is specifically applicable to the 00 type capsule, this ratio would also apply to other size capsules.

In another aspect, the sidewall of the diaphragm which is the straight portion of the diaphragm, and which is cylindrical, extends along the inner surface of the body when the diaphragm is inserted into the body for a distance in the range of 4.5 to 7.5 mm, with an exemplary value of approximately 6 mm.

In another aspect, the overall length of the diaphragm, shown in exploded view in FIG. 4B, is in the range of 7 to 10 mm, again for a typical 00 size capsule with a central or exemplary length of approximately 8.5 mm. Again, note that the nominal length of a 00 size capsule when fully assembled (see FIG. 3B) is approximately 23.5 mm.

Further, in another aspect, the ratio of the sidewall contact length of the diaphragm to the length of the body is approximately 6 mm to 20.2 mm, equal to approximately 0.3. A range of this ratio is approximately 0.22 to 0.37.

As pointed out above, the above parameters and dimensions provide the advantage that the capsule diaphragm, when inserted into the body, during the assembly of the capsule, does not rotate and preserves the capsule's sidewall integrity. Also, these components are configured such that the pressure of the insertion does not need to be too great, thereby preventing a rupture of the capsule during assembly. As noted above, these capsules are such that they are sealed under a certain amount of pressure by the sealing machinery that bonds their components together. Thus a goal here is that the sidewall contact area between the diaphragm and the body allows for optimum alignment of the diaphragm during insertion, resulting in an even edge at the top of the body/diaphragm mouth, providing a good seal both at the body perimeter and its sides. Also, it is intended that this sidewall contact provide adequate friction for the seal, in terms of the overall structure, integrity and robustness of the capsule. Thus, this configuration provides stability and adequate sidewall friction for the seal which advantageously allows for high volume manufacturing with small tolerances. Note that the present sealing process typically includes an application of pressure and heat to bond the gelatin of the capsule components where they overlap, not just a friction fit. In the presently disclosed capsules, the sidewall friction is such that by itself it provides a level of orientation and stability in addition to that provided by the bonding of the components together.

This disclosure is illustrative and not limited; further, modifications and improvements to the disclosed embodiments will be apparent to those skilled in the art in light of this disclosure, and are intended to fall within the scope of the pending claims.

We claim:

1. A multi-compartment capsule comprising:
   a body;
   a diaphragm extending into the body and defining a first compartment between a first surface of the diaphragm and the body, adapted to hold a first ingredient; and
   a cap mounted to the body and opposed to the diaphragm, and defining a second compartment between an opposing surface of the diaphragm and the cap, adapted to hold a second ingredient;
   wherein a sidewall of the diaphragm extends along the body, and a curved portion of the diaphragm is spaced apart from the body; and
   wherein a ratio of the length of the body to the length of the diaphragm is in the range of 2.0 to 2.9.

2. The capsule of claim 1, wherein the ratio is about 2.37.

3. The capsule of claim 1, wherein the sidewall of the diaphragm extends along the body a distance in the range of 4.5 to 7.5 mm.

4. The capsule of claim 3, wherein the distance is about 6 mm.

5. The capsule of claim 1, wherein the length of the diaphragm is in the range of 7 to 10 mm.

6. The capsule of claim 5, wherein the length of the diaphragm is about 8.5 mm.

7. The capsule of claim 1, wherein the capsule is about 23.5 mm in length.

8. The capsule of claim 1, wherein the first compartment is at least partly filled with the first ingredient and the second compartment is at least partly filled with the second ingredient.

9. The capsule of claim 8, wherein at least one of the ingredients is a liquid.

10. The capsule of claim 9, wherein the first ingredient is a liquid, and a remaining portion of the first compartment contains a gas other than air at sub-atmospheric pressure.

11. The capsule of claim 1, wherein the capsule is of a digestible material.

12. The capsule of claim 1, wherein the curved portion of the diaphragm defines a section of a sphere.

13. The capsule of claim 1, wherein a ratio of the length of the sidewall of the diaphragm that extends along the body to a length of the body is in the range of 0.22 to 0.37.

14. A kit of components which assemble to a multi-compartment capsule, the kit comprising:
    a body;
    a diaphragm adapted to extend into the body and thereby defining a first compartment between a first surface of the diaphragm and the body, adapted to hold a first ingredient; and
    a cap adapted to mount to the body and opposed to the diaphragm, and thereby defining a second compartment between an opposing surface of the diaphragm and the cap, adapted to hold a second ingredient;
    wherein a sidewall of the diaphragm is straight and thereby when assembled extends along the body, and a curved portion of the diaphragm extends from the sidewall and thereby when assembled is spaced apart from the body; and
    wherein a ratio of the length of the body to the length of the diaphragm is in the range of 2.0 to 2.9.

15. A body portion of a multi-compartment capsule, the body portion comprising:
    a body; and
    a diaphragm extending into the body and defining a first compartment between a first surface of the diaphragm and the body, adapted to hold a first ingredient;
    wherein the body and diaphragm are adapted to receive a cap mounted to the body and opposed to the diaphragm, thereby defining a second compartment between an opposing surface of the diaphragm and the cap, adapted to hold a second ingredient;
    wherein a sidewall of the diaphragm extends along the body, and a curved portion of the diaphragm is spaced apart from the body; and
    wherein a ratio of the length of the body to the length of the diaphragm is in the range of 2.0 to 2.9.

16. The capsule of claim 1, wherein a mouth of the body and a mouth of the diaphragm are in contact with each other and aligned to form an even edge.

17. The kit of claim 14, wherein a mouth of the body and a mouth of the diaphragm are in contact with each other and aligned to form an even edge.

18. The body portion of claim 15, wherein a mouth of the body and a mouth of the diaphragm are in contact with each other and aligned to form an even edge.

* * * * *